United States Patent [19]

Chapman

[11] 3,983,288

[45] Sept. 28, 1976

[54] FIBERS AND FABRICS CONTAINING OPTICAL BRIGHTENING AGENTS

[75] Inventor: Derek D. Chapman, Rochester, N.Y.

[73] Assignee: Eastman Kodak Company, Rochester, N.Y.

[22] Filed: Nov. 4, 1974

[21] Appl. No.: 520,330

[52] U.S. Cl. ............... 428/260; 252/301.26; 427/158; 428/262; 428/265; 428/267; 428/375; 428/393; 428/394; 428/395; 428/396
[51] Int. Cl.$^2$ .............. B32B 7/00; D02G 3/00
[58] Field of Search ............ 427/158; 428/290, 260, 428/375, 265, 411, 267, 474, 262, 500, 392, 532, 393, 537, 396, 394, 395; 260/290 HL, 290 R, 89.5 S, 88.7 R, 88.7 F, 78 R; 106/143, 195, 204, 186; 252/301.2 W

[56] References Cited
UNITED STATES PATENTS

| | | | |
|---|---|---|---|
| 2,886,569 | 5/1959 | Erner | 260/290 |
| 3,269,955 | 8/1966 | Rodgers et al. | 428/500 |
| 3,322,680 | 5/1967 | Hedbeig et al. | 252/301.2 |
| 3,449,257 | 6/1969 | Tuite et al. | 252/301.2 |
| 3,583,984 | 6/1971 | Crounse | 252/301.2 |
| 3,690,916 | 9/1972 | Wegmuller et al. | 427/158 |

FOREIGN PATENTS OR APPLICATIONS

| | | | |
|---|---|---|---|
| 15,571 | 8/1967 | Japan | 4227/158 |

OTHER PUBLICATIONS

Robinson et al., J. Chem. Soc., pp. 976–982, (1952).
Holland et al., J. Chem. Soc., pp. 1657–1662, (1955).

*Primary Examiner*—Ronald H. Smith
*Assistant Examiner*—Sadie L. Childs
*Attorney, Agent, or Firm*—J. J. Ruch

[57] ABSTRACT

Quaternary salts having a pyrido-[1,2-a]-indole nucleus are useful optical brightening agents for synthetic and natural fibers and fabrics. The quaternary salts are especially useful optical brighteners for paper and acrylic fibers.

24 Claims, No Drawings

FIBERS AND FABRICS CONTAINING OPTICAL BRIGHTENING AGENTS

This invention relates to the use of certain quaternary salts as optical brightening agents for fibers and fabrics.

Fibers, fabrics, films and shaped articles made of paper, cotton, rayon, cellulose, cellulose esters, polyesters, polyamides, polyacrylic resins, polyolefins, polyurethanes, and the like, have an inherent yellowish color which becomes more pronounced as the material ages. The yellowish color is apparent in uncolored or undyed articles made of these materials. In the case of dyed or colored articles made from these materials, the inherent yellow color causes a diminished brightening which becomes more pronounced as the material ages.

Various optical brightening agents are described in U.S. Pat. No. 3,449,257, issued June 10, 1969, U.S. Pat. No. 3,322,680, issued May 30, 1967 and U.S. Pat. No. 3,269,955, issued Aug. 30, 1966.

It is, therefore, an object of this invention to provide novel compositions and shaped articles therefrom which overcome many of the disadvantages of prior art compositions and articles as regards to whiteness and/or brightness.

It is a further object to provide a novel process of brightening fibers and fabrics.

It is still another object to increase the utility of many natural and synthetic materials for use in fibers, fabrics, sheets, films, and other shaped articles by increasing their brightness without concomitant loss of other desirable properties.

It has now been discovered that the brightness and/or whiteness of the materials indicated hereinbefore, can be increased by adding to these materials at least one pyrido[1,2-a]indolium salt. The increased brightness and/or whiteness of these materials is long-lasting and is highly resistant to light, heat, washing, textile-processing baths, dye baths, dry cleaning, bleaching and the like.

The quaternary salts used as the brighteners of this invention are generally described in copending U.S. Pat. application Ser. No. 305,762, filed Nov. 13, 1972 by Chapman, now abandoned and have the formula:

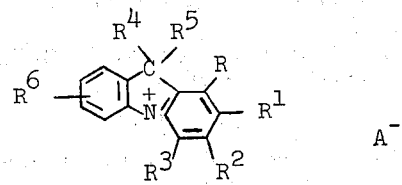

wherein $R^4$ and $R^5$ each represent alkyl, preferably containing from 1 to 12 carbon atoms such as methyl, ethyl propyl, isobutyl, pentyl, octyl, decyl, including substituted alkyl such as chloromethyl, ethylhexyl, benzyl, phenethyl, 2-chloroethyl, 3-hydroxypropyl, 2-methoxyethyl, 3-sulfopropyl, carboxymethyl, ethoxycarbonylmethyl, and the like, or $R^4$ and $R^5$ can, taken together, comprise the atoms necessary to complete a cycloalkyl ring, preferably containing from 4 to 7 carbon atoms such as cyclopentyl, cyclohexyl, and the like; $R^6$ represents a substituent selected from the group consisting of hydrogen, alkyl, preferably containing from 1 to 12 carbon atoms, such as methyl, ethyl, propyl, butyl, hexyl, and the like, alkoxy, such as methoxy, ethoxy, propoxy, butoxy, and the like, aryl such as phenyl, 4-methylphenyl, 2-methylphenyl, 4-chlorophenyl, 4-ethoxyphenyl, tolyl, naphthyl, and the like, aryloxy, such as phenoxy, halogen, such as chlorine, bromine, and the like, cyano, and the like, nitro and fused rings such as benzo, and the like; R and $R^3$ are independently selected from the group consisting of hydrogen and alkyl, preferably containing from 1 to 6 carbon atoms, such as methyl, ethyl, propyl, butyl, and the like or aryl such as phenyl, 4-methylphenyl, tolyl, naphthyl, and the like; $R^2$ represents hydrogen and alkyl, preferably containing from 1 to 6 carbon atoms, such as methyl, ethyl, propyl, hexyl, and the like; $R^1$ represents aryl, such as phenyl, naphthyl, and the like, or a heterocyclic group such as furyl, and the like; $R^2$ and $R^3$, taken together can represent the atoms necessary to complete a carbocyclic ring such as indene, and the like, or a heterocyclic ring such as benzofuro and the like; A⁻ represents an acid anion such as chloride, bromide, iodide, p-toluenesulfonate, thiocyanate, perchlorate, acetate, methylsulfate, ethylsulfate, boron tetrafluoride, and the like.

It is noted herein that alkyl and aryl include substituted alkyl and aryl, wherein the substituents do not adversely affect the desired optical brightening properties, such as alkyl, aryl, alkoxy, cyano, chloro, bromo, iodo, fluoro and the like.

Some examples of salts useful herein are 8-(4-methoxyphenyl)-6,10,10-trimethyl-10H-pyrido[1,2-a]indolium perchlorate, 8-(4-methoxyphenyl)-6,10,10-trimethyl-10H-pyrido1,2-a]indolium chloride, 8-(4-methoxyphenyl)-10,10-dimethyl-6-phenyl-10H-pyrido[1,2-a]indolium perchlorate, 5,8-dihydro-8,8-dimethyl-6-phenylindeno[1',2'-6,5]pyrido[1,2-a]indolium perchlorate, 5,8-dihydro5,5,8,8-tetramethyl-6-phenylindeno[1',2',6,5-]pyrido[1,2-a]-indolium perchlorate, 5,8-dihydro-8,8-dimethyl-6-(2-furyl)indeno[-1',2'-6,5]-pyrido[1,2-a]indolium perchlorate, 8,8-dimethyl-6-(4-methoxycarbonyl)-8H-benzofuro[2',3'-5,6]pyrido[1,2-a]indolium perchlorate, 2-methoxy-8-(4-methoxyphenyl)-6,10,10-trimethyl-10H-pyrido[1,2-a]indolium perchlorate and 6-(4-methoxyphenyl)10,10-dimethyl-8-phenyl-10H-pyrido[1,2-a]indolium perchlorate.

A preferred quaternary salt of this invention has the formula:

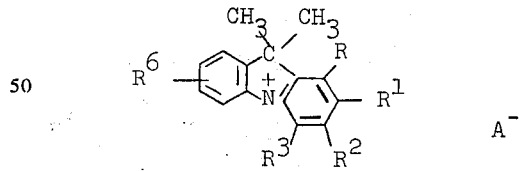

wherein R, $R^1$, $R^2$, $R^3$, $R^6$ and A are as described above.

The novel quaternary salts can be prepared as described in copending U.S. application Ser. No. 305,762, filed Nov. 13, 1972, now abandoned. Generally, a 2-substituted-3,3-dimethyl-3H-indolium salt is reacted with an ethylenically unsaturated ketone. The 2-substituted-3,3-dialkyl-3H-indolium salts which may be used include those having the general formula:

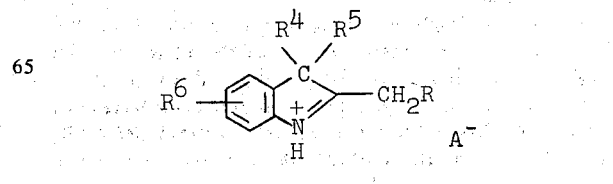

and the ethylenically unsaturated ketones include those having the formula:

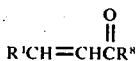

where $R^8$ is lower alkyl such as methyl, ethyl, etc, or aryl such as phenyl, tolyl, naphthyl, biphenylyl, and wherein R, $R^1$, $R^4$, $R^5$, $R^6$ and $A^-$ are as previously defined. The reaction may be conducted in a solvent such as acetonitrile, pyridine, dimethylacetamide or in an excess of the unsaturated ketone reactant. The reaction takes place by heating at the boiling point of the solvent or on a steam bath.

The use of unsaturated ketones in the reaction with 2,3,3-trimethyl-3H-indolium salts is illustrated by the following reaction:

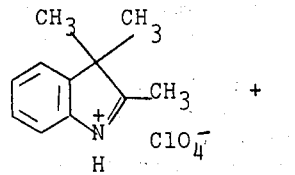

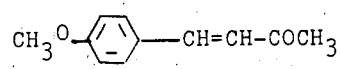

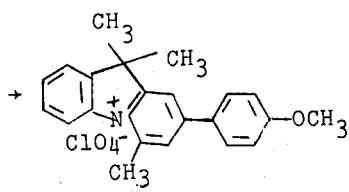

The reaction presumably involves first the nucleophilic attack by the 2-methyl group of the indolium salt on the double bond of the 4-p-methoxyphenylbut-3-ene-2-one followed by cyclization with loss of water to give a dihydro intermediate which is oxidized to give the observed product.

The optical brightener may be incorporated into the fibers, paper, or fabrics in a variety of ways. One method especially useful for treating paper is to incorporate the salt in a hydrophilic binder such as gelatin and coat the brightener and binder onto the material to be treated. Using this method, the concentration of the brightener in the binder is generally from 0.1 to 20% by weight.

Another method of treating fibers or fabrics is to immerse the material in a solution of the brightener in a solvent such as poly(vinyl alcohol), or the like, and boiling for a period of time. The solution generally contains from about 0.05 to about 20% by weight of the brightener.

The optical brightening compositions, in general, can comprise various addenda, such as surfactants, such as the sodium salt of an ether-alcohol sulfate, pH regulators such as phosphoric acid, acetic acid, formic acid, oxalic acid, and the like, and bleaching agents such as sodium chlorite, sodium nitrate, or sodium sulfate.

The optical brightening agents can be used to brighten and/or whiten any fiber or fabric (including paper). Thus, suitable base materials for preparation of the novel articles of manufacture within the scope of this invention include any of the natural or synthetic materials normally used for making fibers, fabrics, sheets, and molded and extruded articles. The optical brightening agents are particularly useful for cellulosic fibers such as paper, acrylic fibers such as polyacrylonitriles (orlon), and the like, polyamide films such as nylon, and like, and many others.

The effective concentration of the optical brightener in or on the fibers or fabrics can be varied widely. In general, it has been found that especially useful results are obtained at concentrations of about 0.01% to about 1.0% by weight of fibers or fabric. A particularly preferred concentration range is from about 0.02% to about 0.5% by weight of fiber or fabric.

The following examples illustrate the preparation of the indolium salts and fibers and fabrics including the brighteners.

EXAMPLE 1

2-Methoxy-6,10,10-trimethyl-8-(4'-methoxyphenyl)-pyrido[1,2-a]indolium perchlorate 5-Methoxy-2,3,3-trimethyl-3H-indolium bromide (1 g.) and 4-p-methoxyphenylbut-3-ene-2-one (4 g.) were heated together on a steam bath for three hours. The cooled melt was triturated with methanol and ether and filtered. The crude product was converted to the perchlorate salt and recrystallized from ethanol. Yield 0.4 g.; m.p. 255°C.

Analysis Calculated for $C_{23}H_{24}ClNO_6$: C, 62.0; H, 5.4; N, 3.1. Found: C, 61.8; H, 5.3; N, 2.9.

EXAMPLE 2

8-(4-Methoxyphenyl)-10,10-dimethyl-6-phenyl-10H-pyrido[1,2-a]indolium perchlorate

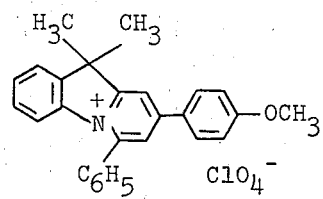

2,3,3-Trimethyl-3H-indolium perchlorate (5 g.) and 3-(4-methoxyphenyl)-1-phenyl-prop-2-ene-1-one (10 g.) were heated together on a steam bath for three hours. The cooled mixture was purified by recrystallization from acetonitrile. The melting point is 258°C.

Analysis Calculated for $C_{27}H_{24}ClNO_5$: C, 67.8; H, 5.1; N, 2.9. Found: C, 67.8; H, 5.3; N, 2.9.

EXAMPLE 3

5,8-Dihydro-8,8-dimethyl-6-phenylindeno[1',2'-6,5]pyrido[1,2-a]indolium perchlorate

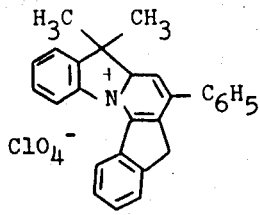

2,3,3-Trimethyl-3H-indolium perchlorate (1 g.) and 2-benzylideneindan-1-one (2 g.) were heated together at 140°–150° for 3 days. The reaction product was dissolved in methanol and then diluted with ether. The product was filtered off and recrystallized from methanol containing Norite decolorizing carbon. Yield 0.9 g.; m.p. 259°–261°.

Analysis Calculated for $C_{27}H_{22}ClNO_4$: C, 70.5; H, 4.8; N, 3.1. Found: C, 70.5; H, 5.1; N, 2.8.

EXAMPLE 4

5,8-Dihydro-5,5,8,8-tetramethyl-6-phenylindeno[1',2',6,5]-pyrido[1,2-a]indolium perchlorate

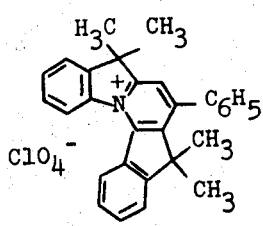

This compound was prepared by the method of Example 4 except that 2-benzylidene-3,3-dimethylindan-1-one was used in place of the 2-benzylideneindan-1-one.

EXAMPLE 5

5,8-Dihydro-8,8-dimethyl-6-(2-furyl)indeno[1',2'-6,5]pyrido[1,2-a]indolium perchlorate

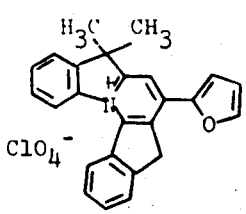

2,3,3-Trimethyl-3H-indolium perchlorate (.7 g.) and 2-(2-furylidene)indan-1-one (14 g.) were heated together for 3 hours at 150°C. The product was isolated after recrystallization of the melt from methanol. Melting point was 229°–230°C.

Analysis Calculated for $C_{25}H_{20}ClNO_5$: C, 66.8; H, 4.5; N, 3.1. Found: C, 66.5; H, 4.8; N, 3.0.

EXAMPLE 6

8,8-Dimethyl-6-(4-methoxycarbonyl)-8H-benzofuro[-2',3'-5,6]pyrido[1,2-a]indolium perchlorate

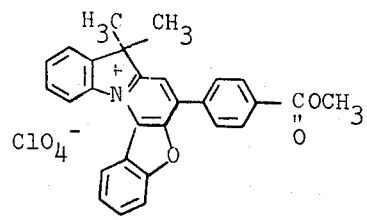

2,3,3-Trimethyl-3H-indolium perchlorate (4 g.) and 2-(4-methoxycarbonyl)benzylidenebenzofuran-3(2H)-one (6 g.) in dimethylformamide (3 ml.) were heated together at 150°C for four hours. The product was isolated by dissolving it in methanol and diluting the solution with ether. It was recrystallized from acetonitrile. Yield 2.3 g.; m.p. 340°C.

Analysis Calculated for $C_{28}H_{22}ClNO_7$: C, 64.7; H, 4.3; N, 2.7. Found: C, 64.8; H, 4.1; N, 2.6.

EXAMPLE 7

6,10,10-Trimethyl-8-(4'-methoxyphenyl)pyrido[1,2-a]indolium perchlorate

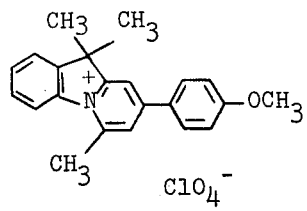

2,3,3-Trimethyl-3H-indolium perchlorate (5 g.) and 4-p-methoxyphenylbut-3-ene-2-one (10 g.) were heated together on the steam bath for three hours. The cooled mixture was diluted with methanol and filtered. The product was purified by recrystallization from acetonitrile. Yield 4.1 g.; m.p. 298°–300°.

Analysis Calculated for $C_{22}H_{22}ClNO_5$: C, 63.5; H, 5.2; N, 3.4. Found: C, 63.7; H, 5.2; N, 3.6.

EXAMPLE 8

8-(4-Methoxyphenyl)-6,10,10-trimethyl-10H-pyrido[1,2-a]indolium chloride

The salt of Example 7 was dissolved in methanol and the solution was treated with an excess of ion exchange resin in the chloride form (Amberlite IRA 400 Resin manufactured by Rohm and Haas Co). After filtration, the filtrate was evaporated to yield the desired chloride salt.

EXAMPLE 9

6-(4-Methoxyphenyl)-10,10-dimethyl-8-phenyl-10H-pyrido[1,2-a]indolium perchlorate

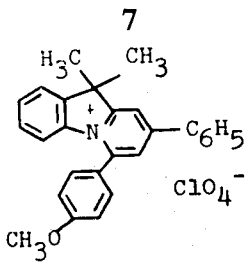

This compound was prepared by the method of Example 3 except that 1-(4-methoxyphenyl)-3-phenylprop-3-ene-2-one was used in place of 3-(4-methoxyphenyl)-1-phenylprop-3-ene-1-one. Melting point was 245°.

Analysis Calculated for $C_{27}H_{24}ClNO_5$: C, 67.8; H, 5.1; N, 2.9. Found: C, 67.5; H, 5.3; N, 2.9.

EXAMPLE 10

Samples of cotton, polyacrylonitrile (Orlon, which is a trademark of duPont Co., U.S.A.) and polyamide (nylon) fabrics were dyed with the salts of Examples 1 through 9 by grinding the brighteners in a stainless steel plate with a small amount of ethylene glycol and an equal amount of poly(vinyl alcohol). The mixture was diluted with water to give a brightener concentration of 1 mg./ml. The fabric samples were immersed in the solution and the solutions were heated to boiling and maintained at that temperature for one hour. The brightened fabrics were compared visually to untreated fabrics and appeared appreciably whiter than the untreated fabrics.

EXAMPLE 11

A polyacrylonitrile fabric (Orlon, which is a trademark of duPont Co., U.S.A.) brightened with the brightener of Example 2 as described in Example 10 was exposed to light in an Atlas Carbon Arc Fade-Ometer for 20 hours and was found to have good resistance to fading.

EXAMPLE 12

The compound of Example 2 was coated at 8.5 mg/ft² of compound in 500 mg/ft² of gelatin on resin coated paper stock. The paper thus treated was examined visually and compared with untreated paper and observed to be much whiter. The treated paper was tested for light fastness by exposing it to simulated afternoon northern skylight (SANS). The whitener was determined to have a half life of 2 weeks.

The invention has been described in detail with particular reference to certain preferred embodiments thereof, but it will be understood that variations and modifications can be effected within the spirit and scope of the invention.

I claim:

1. A nonmetallic synthetic fiber having incorporated therein or thereon from 0.01% to 1% by weight of an optical brightener comprising a quaternary salt having a pyrido [1,2-a] indolium salt nucleus.

2. The fiber of claim 1 wherein the quaternary salt has the formula

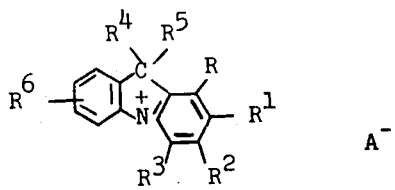

wherein
$R^4$ and $R^5$ each represents alkyl or $R^4$ and $R^5$ can, taken together, comprise the atoms necessary to complete a cycloalkyl ring;
$R^6$ represents hydrogen, alkyl, alkoxy, aryl, aryloxy, halogen, cyano, nitro and fused rings;
R represents hydrogen, alkyl or aryl;
$R^2$ represents hydrogen or alkyl;
$R^1$ represents aryl or a heterocyclic group;
$R^3$ represents hydrogen, alkyl or aryl and in addition $R^2$ and $R^3$ taken together may represent the atoms necessary to complete a carbocyclic or heterocyclic ring;
$A^-$ represents an acid anion.

3. The fiber of claim 1 wherein the quaternary salt has the formula

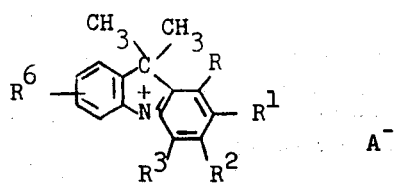

wherein
$R^6$ represents hydrogen, alkyl, alkoxy, aryl, aryloxy, halogen, cyano, nitro and fused rings;
R represents hydrogen, alkyl or aryl;
$R^2$ represents hydrogen or alkyl;
$R^1$ represents aryl or a heterocyclic group;
$R^3$ represents hydrogen, alkyl or aryl and in addition $R^2$ and $R^3$ taken together may represent the atoms necessary to complete a carbocyclic or heterocyclic ring;
$A^-$ represents an acid anion.

4. A nonmetallic fabric having incorporated therein or thereon from 0.01 to 1% by weight of an optical brightener comprising a quaternary salt having a pyrido [1,2-a]indolium salt nucleus.

5. The fabric of claim 4 wherein the quaternary salt has the formula:

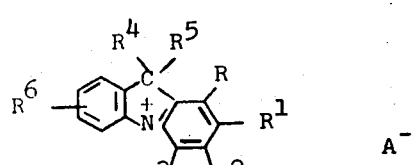

wherein
$R^4$ and $R^5$ each represents alkyl or $R^4$ and $R^5$ can, taken together, comprise the atoms necessary to complete a cycloalkyl ring;
$R^6$ represents hydrogen, alkyl, alkoxy, aryl, aryloxy, halogen, cyano, nitro and fused rings;
R represents hydrogen, alkyl or aryl;
$R^2$ represents hydrogen or alkyl;
$R^1$ represents aryl or a heterocyclic group;
$R^3$ represents hydrogen, alkyl or aryl and in addition $R^2$ and $R^3$ taken together may represent the atoms necessary to complete a carbocyclic or heterocyclic ring;
$A^-$ represents an acid anion.

6. The fabric of claim 4 wherein the quaternary salt has the formula:

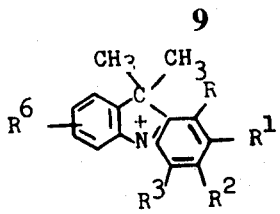

wherein
R⁶ represents hydrogen, alkyl, alkoxy, aryl, aryloxy, halogen, cyano, nitro and fused rings;
R represents hydrogen, alkyl or aryl;
R² represents hydrogen or alkyl;
R¹ represents aryl or a heterocyclic group;
R³ represents hydrogen, alkyl or aryl and in addition R² and R³ taken together may represent the atoms necessary to complete a carbocyclic or heterocyclic ring;
A⁻ represents an acid anion.

7. The fabric of claim 4 wherein the fabric comprises a cellulosic fiber.

8. The fiber of claim 4 wherein the fabric comprises an acrylic fiber.

9. The fabric of claim 4 wherein the fabric comprises a polyacrylonitrile fiber.

10. The fabric of claim 4 wherein the fabric comprises a polyamide fiber.

11. The fabric of claim 4 wherein the fabric is cotton.

12. The fabric of claim 4 wherein the fabric is paper.

13. The fabric of claim 4 wherein the fabric contains the quaternary salt in a binder.

14. The fabric of claim 13 wherein the binder is gelatin.

15. The fabric of claim 5 wherein the fabric contains the quaternary salt in a binder.

16. The fabric of claim 15 wherein the binder is gelatin.

17. A fabric having incorporated therein from 0.01 to 1% by weight of a quaternary salt having the formula:

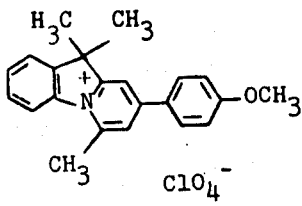

18. A fabric having incorporated therein from 0.01 to 1% by weight of a quaternary salt having the formula:

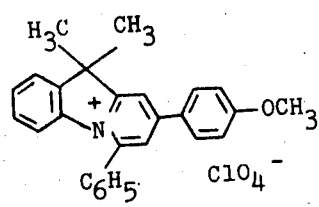

19. A fabric having incorporated therein from 0.01 to 1% by weight of a quaternary salt having the formula:

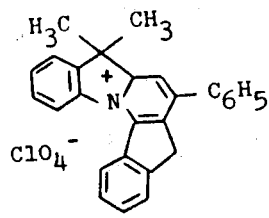

20. A fabric having incorporated therein from 0.01 to 1% by weight of a quaternary salt having the formula:

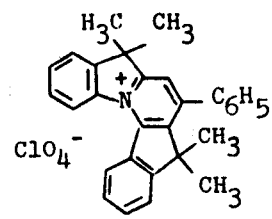

21. A fabric having incorporated therein from 0.01 to 1% by weight of a quaternary salt having the formula:

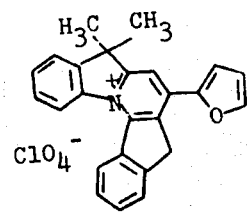

22. A fabric having incorporated therein from 0.01 to 1% by weight of a quaternary salt having the formula:

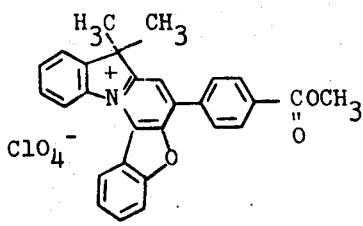

23. A fabric having incorporated therein from 0.01 to 1% by weight of a quaternary salt having the formula:

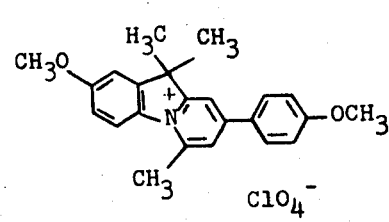

24. A fabric having incorporated therein from 0.01 to 1% by weight of a quaternary salt having the formula:

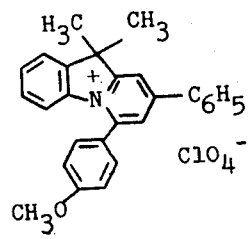

* * * * *